United States Patent [19]

Schulte

[11] Patent Number: 4,469,702

[45] Date of Patent: * Sep. 4, 1984

[54] ANALGESIC COMPOSITION AND USE THEREOF TO AMELIORATE DEEP AND INTRACTABLE PAIN

[76] Inventor: Thomas L. Schulte, 218 Family Farm Dr., Woodside, Calif. 94062

[ * ] Notice: The portion of the term of this patent subsequent to Jan. 18, 2000 has been disclaimed.

[21] Appl. No.: 456,896

[22] Filed: Jan. 10, 1983

Related U.S. Application Data

[63] Continuation-in-part of Ser. No. 276,566, Jun. 23, 1981, Pat. No. 4,369,190.

[51] Int. Cl.$^3$ .................... A61Y 31/10; A61Y 31/235
[52] U.S. Cl. ...................................... 424/308; 424/337
[58] Field of Search ............................... 424/308, 337

[56] References Cited

U.S. PATENT DOCUMENTS 3,551,554  8/1968  Hershler ............................. 424/337
4,073,897  2/1978  Karlor ................................ 424/230

Primary Examiner—Stanley J. Friedman
Attorney, Agent, or Firm—Millen & White

[57] ABSTRACT

Deep and intractable pain is ameliorated by the topical application proximate the situs of the pain of an analgesic amount of an aqueous mixture of biphenamine and a water soluble skin penetrant, e.g., DMSO or propylene glycol, in a pharmaceutically acceptable carrier, the concentration of biphenamine and skin penetrant in the mixture each being ineffective to ameliorate the pain when applied separately from the other to the situs. The mixture is also useful for the amelioration of pathological conditions of the skin and other topical areas of the body, e.g., those caused by viral, bacterial, fungal and other microorganism infections and those having associated localized inflammatory response which cause itching or pain, e.g., wounds and burns.

14 Claims, No Drawings

ANALGESIC COMPOSITION AND USE THEREOF TO AMELIORATE DEEP AND INTRACTABLE PAIN

BACKGROUND OF THE INVENTION

This is a continuation-in-part of application Ser. No. 276,566, filed June 23, 1981, now U.S. Pat. No. 4,369,190.

This invention relates to novel topical analgesic compositions and to their use to alleviate deep pain and debriding wounds and enhancing the healing thereof.

The treatment topically of deep or intractable pain, i.e., pain non-responsive to local anesthetics, with analgesics historically has not met with significant success, primarily because the surface presented by the affected area, typically skin or mucous membrane, provides an effective barrier to the analgesic agent reaching the situs of the pain. Therefore, physicians must resort to injections to achieve absorption of the analgesic, which usually also requires that the analgesic agent be in a vehicle which retards the rate of absorption, or to the oral administration of systemic analgesic agents, such as the barbituates. Both of these approaches have obvious limitations and pose well-known problems. There therefore is a long standing need for an effective topical analgesic agent which is effective in ameliorating localized deep or intractable pain and can safely be applied to the situs of the pain by the person in pain.

The compositions of this invention comprise biphenamine (β-diethylaminoethyl 3-phenyl-2-hydroxybenzoate) base or pharmaceutically acceptable acid addition salt thereof. Salts of this compound are known to have a variety of activities, including local anesthetic (U.S. Pat. No. 1,976,922); treatment of seborrhea (U.S. Pat. No. 3,123,531); as well as antihistaminic and bactericidal activity and fungicidal properties (U.S. Pat. No. 2,594,350; Report Annual Meeting So. Med. Assoc., Nov. 6, 1961).

Biphenamine hydrochloride has been sold as a 1% ointment, under the trademark "Melsaphine," as a topical anesthetic agent possessing bactericidal, fungicidal and antihistamine properties and as a 1% aqueous shampoo under the trademark "Alvinine," Federal Register, Vol. 34, No. 189, page 153, Oct. 2, 1969. See also U.S. Pat. No. 3,123,531.

Although its use orally or subcutaneously for treating arthritis and related conditions is claimed in U.S. Pat. No. 4,073,897, nothing was known concerning its topical analgesic activity or its usefulness for the treatment of localized deep or intractable pain because the compound is ineffective for ameliorating deep or intractable pain by the topical application thereof, in the absence of a tissue penetrant.

The compositions of this invention also comprise an amount of a skin penetrant, e.g., DMSO (dimethyl sulfoxide) or propylene glycol, which by itself has no analgesic activity or debriding or wound healing enhancement effects. U.S. Pat. Nos. 3,551,554 and 3,711,602 disclose that DMSO is effective as an agent for enhancing tissue penetration of physiologically active agents. U.S. Pat. No. 3,549,770 discloses (Example 36) the topical application of a mixture of acetylsalicylic acid and DMSO is more effective than DMSO alone to relieve the pain and muscle spasm of rheumatoid spondylitis. See also U.S. Pat. Nos. 3,711,602; 3,711,606; and 3,743,727 and references cited therein. These patents disclose that the tissue penetration of physiologically active compounds, inter alia, steroidal agents and certain antimicrobial agents, can be enhanced by DMSO. U.S. Pat. No. 3,740,420 discloses DMSO compositions for topical administration containing thickening agents.

The foregoing patents disclose that concentrations of DMSO of 10% by weight and above can effect penetration of such agents through various mucous membrane barriers and that concentrations of 50% by weight and above are effective to achieve penetration thereof through the skin. DMSO is also known to enhance the antiperspirant activity astringent of aluminum, zinc and zirconium salts (U.S. Pat. No. 3,499,961).

DMSO has been disclosed as useful for treating a variety of pathological conditions. U.S. Pat. No. 3,549,770 discloses topical application as a particularly advantageous route. This patent claims methods of relieving the signs and symptoms of tissue inflammation; of vascular insufficiency in the blood and lymph circulatory system; of respiratory distress; of arthritis and a method of promoting tissue repair, by administering an effective amount of DMSO, preferably topically. Dosages as low as 0.01 g/kg and up to 1.0 g/kg per day and sometimes higher dosages are contemplated with 0.1–0.2 g/kg individual doses being average. Higher concentrations of DMSO, such as at least 25% and more often at least about 50% are preferred for topical application. Treatment of pain with such solutions of DMSO, preferably by direct application to the involved area, is expressly contemplated. In one example (Example 27) the pain associated with skin abrasion was relieved with 15% DMSO in isotonic saline. 10% to 90% water solutions of DMSO, preferably 20% to 40%, in water, alcohol or glycerine are useful for topical application to the mucous membranes of the body although ". . . lower concentrations of DMSO say down to 3% by weight may be useful in some instances."

The use of DMSO as an ataratic agent is disclosed in U.S. Pat. No. 3,790,682. Pharmaceutical compositions containing DMSO and thickening agents are disclosed in U.S. Pat. No. 3,740,420, along with their use to treat and repair damaged tissue, as an anti-inflammatory agent, as an analgesic agent, as a muscle relaxant, as an agent for treating vascular insufficiency, and relieve the signs and symptoms of certain specific syndromes, viz., respiratory distress, arthritis and burns. None of the foregoing references disclose or suggest that intractable pain can be treated with low concentrations of DMSO, e.g., topically on the skin at concentrations below 10%, although U.S. Pat. No. 3,549,770 discloses (Col. 10, lines 42-49) that for pharyngitis or hiccups, the subject may gargle with a more dilute aqueous solution, e.g., containing 1% or preferably 10% by weight of DMSO, and (Col. 28, lines 44-56) that concentrations of DMSO down to 3% by weight may be useful in some instances, with 10% to 90% water solutions being particularly suitable. The effectiveness of DMSO topically for treating pain at concentrations below 10% by weight is not suggested in the prior art. Moreover, I have found that low concentrations of DMSO alone have little if any effect topically upon intractable pain. Propylene glycol has no analgesic activity at any concentration.

SUMMARY OF THE INVENTION

In a method of use aspect, this invention relates to a method for amelioration of deep pain which comprises applying topically proximate the situs of the pain an analgesically effective amount of an aqueous mixture of biphenamine and a water soluble topically acceptable skin penetrant in a pharmaceutically acceptable carrier, the concentrations of biphenamine and skin penetrant in the mixture each being ineffective to ameliorate the pain when applied separately from the other to the situs.

In a composition aspect, this invention relates to an analgesic composition adapted for topical administration and comprising an aqueous mixture of biphenamine and a topically acceptable skin penetrant in a pharmaceutically acceptable carrier, the concentrations of biphenamine or salt thereof and the skin penetrant in the composition being collectively effective to render the composition capable of ameliorating intractable pain when the composition is applied topically proximate the situs of intractable pain but ineffective for either component of the composition to do so in the absence of the other.

DETAILED DISCUSSION

The aqueous mixture of biphenamine (base or acid addition salt thereof) and the skin penetrant are applied topically to the patient proximate the suits of the deep pain, viz., to the skin and/or the mucous membrane of the mouth, throat, nasal passages, ear canals and drums, anal or vaginal regions, bladder or urethra, as a mixture in a pharmaceutically acceptable carrier or diluent, preferably aqueous. The mixture preferably is liquid, e.g., in the form of clear solutions, such as drops, aerosols or sprays, or in the form of lotions or other viscous aqueous liquids. The mixture can also be semi-solid or solid, e.g., in the form of ointments, creams, suppositories. Viscosity regulating agents, such as thickeners and gelling agents, e.g., glycerin, sodium carboxymethylcellulose, etc., can also be used to regulate flowability. See U.S. Pat. Nos. 3,740,420 and 3,711,602, whose disclosures are incorporated herein by reference. Propylene glycol itself is useful as a viscosity raising agent. They can be in the form of an oil-in-water or water-in-oil emulsion, as disclosed in U.S. Pat. No. 3,740,420, or as a single phase aqueous solution, the latter being preferred. Organic solvents, e.g., ethanol or isopropanol, can also be present.

The skin penetrant is present in the mixture at a concentration of at least about 1% which is not analgesic topically in the absence of the biphenamine. DMSO is employed at concentrations of less than 10%, e.g., 3-7%, preferably about 5%. At these concentrations, DMSO exhibits neither the analgesic effect achieved when it is applied to the skin in the absence of the biphenamine nor the side effects observed at higher concentrations, e.g., skin rash. Propylene glycol is employed at concentrations of about 1% to 90%, preferably about 5% to 15%, more preferably about 10%. Propylene glycol has desirable emollient and thickening qualities, which therefore makes it preferable in some formulations and with some patients.

The biphenamine is present in the liquid mixture at a concentration of up to 1% by weight, e.g., from about 0.1% to 1%, except for instillations, where lower concentrations of about 0.001 to 0.01% should be employed, preferably present in the form of a pharmaceutically acceptable salt thereof, e.g., hydrochloride, hydrobromide, sulfate, phosphate, acetate, succinate, tartrate, benzoate, citrate, lactate or maleate, preferably the hydrochloride. Although acid addition salts of biphenamine are disclosed in U.S. Pat. No. 1,976,922 as having local anesthetic activity at a 2% concentration, neither its ability to ameliorate localized intractable pain when applied topically nor its effectiveness on the skin for any purpose at lower concentrations is suggested.

The mixture of biphenamine and skin penetrant can be applied topically as frequently as every hour or as infrequently as daily or longer, depending on the degree of amelioration of the pain achieved with each application and the duration thereof. In the case of burns, it is desirable to apply the mixture promptly after the burn occurs and on successive occasions thereafter, e.g., once every 2-12 hours for 2-14 days or until the burn is healed.

The amount of the mixture applied will depend on such factors as the level and nature of the pain, the degree of localization thereof, the concentration of biphenamine and skin penetrant therein and the individual's responsiveness to analgesics generally. As little as two or three drops may be effective and as much as a fluid ounce may be required. The effectiveness of successively greater or smaller dosages can determine the optimum effective individual dose. The mixture can be applied to small areas with an eye dropper or a piece of cotton and to larger areas as a spray or aerosol or with a surgically gloved hand.

The compositions of this invention are effective for the amelioration of deep pain, i.e., pain non-responsive to local anesthetics, e.g., structural pain associated with influenza and other infectious diseases, arthritis, bursitis, tendonitis, trauma pain, e.g., strains, such as pulled muscles, and sprains, and other forms of intractable pain, i.e., pain which is substantially non-responsive to non-sedating systemic analgesics such as aspirin, phenacetin and acetaminophen. The method of this invention is useful for the treatment of localized intractable pain resulting from a wide variety of pathological conditions, e.g., severe sprains, debriding wounds, degenerative disc syndrome, bursitis and severe thermal or traumatic burns. From clinical observations, when a composition of this invention is applied to the affected area promptly after a skin burn and on successive occasions thereafter, not only is pain ameliorated or eliminated, the healing process is facilitated, apparently by the suppression of the inflammatory response and infection. The compositions of this invention are also useful for the amelioration of pathological conditions of the skin and other topical areas of the body caused by viral, bacterial, fungal and other microorganism infections and localized inflammatory conditions generally which cause itching or pain, e.g., herpes virus lesions, pain, itching and fungus infections of the perineum, feet, hands, ear canal, inflammation or sclerosis of the ear drum, urinary bladder, urethra, abscess cavities, leg ulcers, bed sores, infected sinuses, senile keratosis, animal and insect bites, painful muscle spasms and pain from "pinched nerves."

It is postulated on the basis of studies at the cellular level that enzyme imbalances cause physiological abnormalities which are corrected according to this invention by the skin penetrant carrying the biphenamine to the situs of the abnormality. Consequently, in addition to ameliorating the pain associated with wounds and burns, the healing thereof is facilitated by the compositions of this invention by the suppression of the inflammatory response. Additionally, the biphenamine inhibits infection of the situs of the wound and debriding of dead or injured tissue.

Although biphenamine hydrochloride as a 1% ointment is known to be useful for the treatment of minor burns, minor skin irritations or insect bites and to have bactericidal, fungicidal and antihistiminic properties at that concentration, it is surprising that concentrations thereof of only about 0.1% are equally or more effective when employed as an aqueous mixture with a skin penetrant such as DMSO or propylene glycol. Although U.S. Pat. NO. 2,594,350 teaches that a 0.14% solution of the mandelic acid salt of biphenamine is useful as a urinary antiseptic and germicide, the activity thereof is due in part to the known urinary bactericidal activity of mandelic acid.

Contemplated equivalents of the compositions and methods of treating pain of this invention are compositions otherwise corresponding thereto containing a different topically acceptable skin penetrant, in place of the DMSO or propylene glycol, and the use thereof topically to treat intractable pain.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The following are examples of compositions of this invention.

EXAMPLE 1 a. An aqueous solution of DMSO and biphenamine hydrochloride can be produced by dissolving 50 grams of the former and 1 gram of the latter in 950 cc of sterile isotonic water. The viscosity thereof can be increased with any conventional viscosity enhancing agent, e.g., carboxymethylcellulose.

b. A solution of propylene glycol and biphenamine hydrochloride can be prepared by mixing 10 grams of the former with 900 grams of sterile water containing 1 gram of the latter dissolved therein. The propylene glycol acts as a viscosity enhancing agent, producing a viscous solution.

EXAMPLE 2 a. A lotion can be formulated in the conventional manner from the following ingredients, after dissolving the biphenamine hydrochloride and buffer in the water.

| Biphenamine · HCl | 1 gm |
|---|---|
| DMSO | 50 cc |
| Cetyl alcohol | 200 gm |
| Propylene glycol | 100 gm |
| Sodium laural sulfate | 15 gm |
| Water q.s. 1000 cc | | b. The above lotion can also be prepared with the DMSO omitted therefrom.

EXAMPLE 3 a. An ointment can be produced from the following ingredients, after dissolution of the biphenamine hydrochloride in water.

| Biphenamine · HCl | 1 gm |
|---|---|
| DMSO | 50 cc |
| Glyceryl monostearate, Acid Type | 180 gm |
| Stearyl alcohol | 50 gm |
| Polysorbate 80 | 20 gm |
| Water q.s. 1,000 cc | | b. An ointment can also be prepared in which the DMSO is replaced by 50 grams of propylene glycol.

EXAMPLE 4 a. An aqueous alcoholic ointment can be prepared by blending the following ingredients, with the biphenamine hydrochloride first dissolved in the water.

| Biphenamine · HCl | 100 mg |
|---|---|
| DMSO | 5 gm |
| Ethanol | 10 gm |
| Corbowax 1,500 | 20 gm |
| Water q.s. 1,000 | | b. An ointment in which the DMSO is replaced by 10 gm of propylene glycol can similarly be prepared.

EXAMPLE 5 a. Suppositories can be cast from a melt of the following ingredients, after first dissolving the biphenamine hydrochloride in the water.

| Biphenamine · HCl | 70 mg |
|---|---|
| DMSO | 3.4 gm |
| Sodium stearate | 10 gm |
| Glycerin | 45 gm |
| Water | 10 gm | b. Suppositories in which the DMSO is replaced by 7 gm of propylene glycol can also be produced.

The following examples illustrate the method of this invention.

EXAMPLE 6

The acute pain resulting from collapsed discs in the neck of a female age 71 was successfully ameliorated for periods of 1 to 10 hours by the topical application of 1 to 16 drops of the composition of Example 1a to the occiput, the situs of the pain. As a result, the necessity of traction and the wearing of a neck collar which immobilized the neck was eliminated.

EXAMPLE 7

A male age 68 who experienced consistent severe lower back pain after a lumbar disc operation had attempted to no avail to alleviate the pain variously with Percodan, aspirin, 90% DMSO applied topically to the lower back region, and alcohol consumption. Within eight minutes after the application of 8 drops of the composition of Example 1a topically with manual spreading around the lower back at the situs of the pain, the pain was gone and remained eliminated for 8 days. The patient used the composition in this manner off and on at various intervals and found the relief from pain superior to 90% aqueous DMSO, with none of the redness or skin irritation associated with the use of the latter.

The same superior results were achieved with this patient in relieving the pain associated with a sprained knee which was swollen and the knee could not be bent. Several drops of the composition of Example 1a spread around the knee area produced marked relief from the pain occurring within a few minutes. Movement of the knee was possible within a few hours thereafter.

EXAMPLE 8

A 78 year old arthritic patient with a painful knee of unknown etiology obtained immediate relief from the pain after a few drops of the composition of Example 1a was spread on the knee area. Previously, 90% aqueous DMSO had been tried by the patient without much relief.

EXAMPLE 9

The index finger of a 38 year old woman had been damaged by an automatic riveting gun, resulting in severe pain and infection of the tendon. Although treatment with 90% DMSO had given some relief, after 9 months she had limited motion in the finger and the pain precluded her use of the riveting gun. Within 24 hours after applying a few drops of the composition of Example 1a to the injured finger, it could be extended nearly to normal position without pain. After repeated treatments over a period of about 2-3 weeks, she had normal movement of the finger without pain.

EXAMPLE 10

A 74 year old artist had such severe bursitis in his right shoulder that he could not paint. He obtained relief from the pain after one application of several drops of the composition of Example 1a to the shoulder area and was able to drive several hundred miles in his automobile. Upon his return, the bursitis flared up again but the pain was ameliorated by a second application.

EXAMPLE 11

A male (66 years) had a virus respiratory and intestinal infection that did not respond to treatment, including vertigo medicine, either for infection or for dizziness. After 6 weeks he was still suffering and toxic and had a sore inflammed throat. He placed a few drops of the composition of Example 1a in his ears and after 2 hours he put ½ teaspoon (2cc) thereof in a quarter glass of water and gargled with the mixture. Overnight he was greatly improved. He repeated the treatment after 24 hours and 48 hours. He required no further treatment and remained free of symptoms.

EXAMPLE 12

A female (43 years) developed symptoms and clinical condition similar to those of Example 11. Her doctor examined her ears, nose and throat as part of a general physical examination. He also prescribed medication for the dizziness and respiratory and intestinal symptoms, but the condition remained. Drops of the composition of Example 1a were inserted into each ear canal, once a day for 5 days. After the first day, the patient was relieved of the symptoms and after stopping the treatment, the symptoms did not reoccur.

EXAMPLE 13

A male (78 years) had buzzing or ringing in the ears (tinnitus) for 50 years. All treatments and medicines failed and the symptoms became increasingly bothersome with age. All treatment failed. He also had a fungus infection in both ear canals. Drops of the composition of Example 1a were applied 4 times in one day, from late afternoon until bedtime. The next morning there was a change in the tone of the tinnitus which appeared to be ameliorated by the treatment.

EXAMPLE 14

A male (39 years) twisted his spine and displaced a thoracic disc in his back while riding a horse. He developed a severe spasm and swelling of the erector spinae muscles on the left side of his back. He had to lie flat on his back to relieve the pain and could not walk without stooping over. The composition of Example 1a was applied to the area of tenderness in his back. Within 15 minutes there was a definite improvement in the severity of the pain. Another application was made ½ hour later and a third 1 hour after that. He developed a slight redness at the site of application, which appeared to be the result of an increase in the capillary circulation rather than an irritation of the skin. There was no pain, no itching, no burning and no discomfort and he was entirely comfortable.

The following examples illustrate the use of compositions of this invention to ameliorate the pain associated with wounds and burns and the promotion of the healing thereof.

EXAMPLE 15

A construction worker received a ragged cut from a saw which was approximately two cm. long and about one cm. deep on the medial portion of the left hand. The wound bled profusely and was very painful. First aid was instituted and the bleeding was stopped. The wound was disinfected and a tetanus shot administered. The wound was very painful for several days. Aqueous propylene glycol (10%) was applied to keep the wound pliable but there was no improvement and the pain persisted. Then a solution of Example 1b was applied and relief of pain, which was observed within approximately 20 minutes, persisted for 4 hours. The same solution was again applied and was used over the course of the healing with application about every 4 hours. The wound healed without any further complications or further pain.

EXAMPLE 16

A female (72) patient developed acitinic keratitis, which corresponds to senile keratosis and is a precursor to squamous epithelioma. A dermatologist diagnosed and treated the condition with 5-flurouracil topically, which produced an intensely inflammed area with redness and pain. After the treatment was completed, an inflamed red area remained which was painful, swollen and unsightly. The application of the solution of Example 1a resulted in immediate relief of pain. After several days the lesion disappeared and the skin appeared normal. Pain did not reoccur since the first application.

EXAMPLE 17

A female (15) with severe sunburn over her front and back applied the solution of Example 1a to the back but not the front. The pain and inflammation disappeared promptly from the back but naturally persisted in the front, which was treated with an oily emollient solution which was ineffectual by comparison.

EXAMPLE 18

A female (20) with a severe sunburn to the entire body applied the solution of Example 1a to the left arm and shoulder and applied conventional medication to the other arm and shoulder. The former area was promptly relieved of pain whereas the right side was only slightly improved.

EXAMPLE 19

A male (63) with severe sunburn to face and chest treated one side of his face and one side of his chest with the solution of Example 1a and the other sides with conventional sunburn medication. There was an immediate improvement in the former areas whereas the latter areas were only slightly improved. The following day the former areas were normal and the latter areas were still inflamed and tender.

EXAMPLE 20

A female (72) spilled hot grease over the back of the left hand. Pain was severe. Immediately (2 min.) after the burn, the solution of Example 1a was applied to the burn area. Pain disappeared in 3-5 minutes and never recurred. Twelve hours later, no blister had appeared. The solution was again applied to the burn area. The epithelial skin was darkened by the burn but there was neither blistering nor pain. The solution was applied 2-3 times daily for 7 days. On the 7th day, the dead epithelium flaked off leaving slightly pinker than normal skin underneath. In 10 days, the burned area was normal. There never was any pain, blister, cracking of the tissues or exudation of tissue fluid. Slight pigmentation was the only residual effect of the burn.

EXAMPLE 21

A male (73) was burned by the sharp corner of a red hot iron door of a Finnish Sauna oven left ajar, which branded the lateral mid-thigh on the left side. There was the odor of burnt flesh and intense pain. The solution of Example 1a was applied topically to the burned area within 1 minute of the burn and spread around the area. Within 3 minutes, there was no further pain. The solution was applied again several times over the next hour. After 12 hours, there still was no pain. No blister appeared but there was an obvious brand where the hot iron had penetrated the tissue. Further applications of the solution was made on 2 or 3 occasions the day of the burn and the day following, although they did not seem necessary because of the lack of pain. However, because the branding was so severe, the treatment was repeated, although there never was any further pain or blistering. The only evidence of the burn was a brand the shape of a V, where the corner of the red hot door made pressure contact with the tissue, and a wedge-shaped area below the branded area which appeared to be similar to the ecchymosis following trauma. However, the difference was that in the case of ecchymosis of trauma there is a more diffuse and rounded appearance to the ecchymotic area. The brownish wedge shaped area on the dependent side of the brand was outlined sharply, as if cut out of a piece of paper or cloth with straight sides coming together to form a point. It is assumed that this discoloration was the result of the tissue damage caused by the brand and the tissue fluids which diffused by gravity dependently. Presumably because of the immediate application of the solution of Example 1a, there was no diffuse area of tissue damage surrounding the brand. After 10 days, the burn was healed and the brownish discoloration proximate the branded area returned to its normal color, except a slightly bluish hue.

EXAMPLE 22

A male (45) welder, who was welding a heavy iron rod, picked up the rod in his bare hands to put it on the table on which he was working. He inadvertently picked up the hot portion of the rod, which promptly branded his hand. Immediately (within 1-2 minutes) he applied the solution of Example 1a and spread it over the palm of the hand and between the fingers. He was seen the following day. There was no evidence of any burn and no blistering, except for a small area between the fourth and fifth fingers where he neglected to apply the medication. There never was any pain although the solution was applied only once immediately after the burn.

EXAMPLE 23

A male (43) smoking a cigarette accidentally pinched the lighted end of the cigarette between his fingers as he was attempting to remove the cigarette from his mouth. The solution of Example 1a was applied within 2 minutes. The pain was relieved in a few minutes and no blister developed. There was no pain on the following day and the burn was healed in one week, although there was slight pigmentation in the area which lasted several months before disappearing.

EXAMPLE 24

A boy (6) fell from a horse, striking his face and head on the gravelled road. This resulted in a deep ithelization of the skin and a traumatic burn into the subcutaneous tissues of the face and forehead. The boy was in mild shock and severe pain but was able after some time to return home, which took 2 hours. Once home, the solution of Example 1a was applied to the traumatized area by the child himself because he would not let anyone touch him. There was no cleaning or disinfection of the area because the child would not permit it. Instead, he applied the solution to himself liberally with cotton. In 20 minutes the boy fell asleep and awoke the next morning with swelling of the face and forehead but a minimal of pain. He permitted someone else to apply the solution again to the affected areas. Although these two applications were the only ones, there was no further pain and there was no infection that developed. After several weeks of healing, there was no scarring, pigmentation or other abnormality.

EXAMPLE 25

A male (23) playing soccer fell while running and skidded on the dry ground on his thigh, resulting in a burn that took off the skin and exposed a raw bleeding area. After a shower and soap and water (about 1 hour after the injury), the solution of Example 1a was applied to the traumatized area. There first was a slight burning sensation followed a few minutes thereafter by complete relief of pain. The solution was applied again later the same day and the following morning. This was the only treatment. There was normal healing, no infection, never any pain and after the usual pigmentation resulting from such a trauma, this disappeared after a few weeks without scarring or evidence of injury.

EXAMPLE 26

A male (23) polo player took a spill going at a speed of about 30 miles an hour and skidded on the turf landing on his shoulder, arm, forearm and side of the face and received severe burns. Following the game, a shower, soap and water and cleaning the affected areas, the solution of Example 1a was applied to all the affected areas except the forearm, which was used as a control. The areas where the solution was applied resulted in relief of pain in a few minutes whereas the area untreated on the forearm continued to be painful and did not heal as quickly as the areas where the solution had been applied.

The following examples illustrate the healing and/or pain relieving effect of the compositions of this invention.

EXAMPLE 27

Several species of animals, viz., horses, dogs and cats, had severe traumatic penetrating and secondarily infected wounds. Most were foul smelling. Some were burns due to ropes, cinches, straps or saddle sores and assorted causes. The topical use of the solution of Example 1a was effective in all cases in debriding and cleaning the infected areas and promoted healing without leaving angry appearing granulation tissue.

EXAMPLE 28

A female (72) with a mosquito bite on the base of the right thumb was treated with the solution of Example 1a. Relief of itching was observed but a spread of the noxious material from the bite occurred and there was a continuation of the itching to a minor degree. On the following day a similar bite on the other thumb in the same place was treated with the solution of Example 1b. The propylene glycol (10%) did not cause spread of the noxious material from the bite and there was a complete relief of itching which was much more marked than with the bite treated on the other thumb.

EXAMPLE 29

A female (70) with dermatitis of unknown etiology on the upper outer leg with raised areas that itched considerably was treated with a solution of Example 1b which gave prompt relief of the itching and swelling.

EXAMPLE 30

A male (58) cut himself at the base of the left thumb with a chain saw. The area was extremely painful at the site of the cut and in the surrounding area. The application of the solution of Example 1b relieved the pain, especially in the areas of trauma around the cut area. The following morning, there was very little pain and reapplication resulted in disappearance of all pain. There was prompt and complete healing without infection or residual soreness.

EXAMPLE 31

A pastured horse received a penetrating wound that became infected and fly blown with maggots falling out of the wound and the odor was bad enough so that none of the grooms would go near the horse. The wound was about six inches deep and about eight inches wide. The serum had exuded from the wound as is the case in horses with an open would that leaks serum and tissue fluid and the hair inferior to the wound was missing due to the action of the tissue fluid exuding from the wound. The solution of Example 1a was injected into the wound until it filled the wound and the excess ran out over the area that had been epilated. Within a few minutes the offensive odor was gone. The treatment was repeated daily, there was no odor, no maggots, no attraction to flies and the wound healed cleanly without leaving any granulation tissue that usually accompanies such a wound in the horse. The area where the hair was lost promptly grew back and the wound healed without leaving an ugly scar.

EXAMPLE 32

A 3-year old female Laborador ran in front of an automobile, which braked and then ran over the left forefoot of the dog and dragged it along the gravel road for a distance of 20 feet, before stopping and backing off the dog's foot. The dog was immediately taken to a veterinarian who treated the dog and bandaged it tightly as well as treating with antibacterial medication. The following day there was a great amount of pain and swelling and the dog was taken to his regular veterinarian, who removed the pressure dressing and examined the damaged foot. The entire skin of the top, sides and bottom of the foot was missing. The pads on the bottom of the foot were also missing and there remained a raw swollen mass that was obviously quite painful and the dog whimpered whenever any part of the foot was touched. Thereafter, the only treatment was the solution of Example 1a which was applied daily and a loose bandage was applied. The dog naturally walked on 3 legs for some time. After several days no bandage was used and the solution was applied from time to time but not at regular intervals. After a few weeks the dog's foot was normal.

Pain was relieved by the solution, as evidenced by the fact that the dog did not whimper when the loose bandage was applied or when the foot was touched when examined or when the solution was applied and rubbed on the area. There never was any infection and the area healed completely, including regrowth of the foot pads and the nails that had been lost.

The following examples illustrate the use of the solutions of this invention by instillation.

EXAMPLE 33

On the basis of animal experimentation and because of the established safety of the solution of Example 1a by various routes of administration including orally, that solution was used to treat patients with interstitial cystitis. This is an extremely painful inflammatory condition of the urinary bladder which is thought to be an autoimmune disease and for which there is no cure. At times it is necessary to remove the bladder because of intractable pain. DMSO as a 50% solution is approved by the FDA for this condition.

A female (38) had a confirmed diagnosis of interstitial cystitis which was refractory to all treatment, including several courses of DMSO. Cortisone had also been administered intramurally (injected into the bladder wall) with only temporary benefit. Before considering cystectomy, it was decided to administer by local instillation topically the solution of Example 1a. Despite the prior intractable nature of her condition, the patient was relieved of her pain for several weeks. Following a second local instillation, there was a relief of pain for a longer time. The intervals of relief of pain increased with each application of the solution. Although her condition was not cured, the topical local instillation was a definite benefit to the patient.

EXAMPLE 34

A female (58) with recurring hemorrhoids and rectal fissures with severe pain and itching was treated by the topical application of the solution of Example 1a. Pain and itching were relieved promptly.

EXAMPLE 35

A male (65) with severe hemorrhoids and a severe fungus infection of the area of the anus and perineum was treated by topical application of the solution of Example 1a. Pain and itching were relieved although the fungus infection had been present for many years and there was never any relief, in spite of frequent bathing and changing underwear twice or more daily.

EXAMPLE 36

A female (49) following a removal of the left kidney, developed a fecal fistula post operatively. The fecal material and flatus passed copiously from the sinus. Prior to considering surgical treatment, the wound was cleansed with the solution of Example 1a. Surprisingly, not only was a debriding effect achieved and a clean wound obtained, the fistula healed and closed in 3 days.

EXAMPLE 37

A mare (12 years) with a severe uterine infection and a purulent discharge from the uterus had been treated with all known medications for infections by systemic and local administration including intrauterine packs of antibacterial drugs, in an attempt to clear up the infection prior to considering the possibility of getting her in foal. Her condition was noted by the farm manager, a verterinarian and several grooms, all of whom had seen and examined the mare previously on many occasions, including a speculum inspection of the cervix to determine her present condition. Thereafter, the solution of Example 1a was instilled into the mare's vagina on three successive occasions. Two weeks later, the mare was found to be clean and the infection which had been refractory to all other treatment was gone.

EXAMPLE 38

A female (44) with a severe infection of the cervix uteri refractory to other treatment took a vaginal douche using the solution of Example 1a diluted with one tablespoonful of 1000 cc water. This was repeated once in 24 hours. After 2 weeks there was no evidence of infection or inflammation. This treatment was repeated on several cases and always improved the patient's condition.

The following examples illustrate the use of the compositions of this invention for the treatment of respiratory and sinus inflammation and allergies.

EXAMPLE 39

A mare (3 years) had been roaring and bleeding on the race track as a result of the stress of racing. The solution of Example 1a was sprayed into the nostrils once with complete relief of roaring and no bleeding as the result of racing. Thereafter, she won several races and was never ruled off the track because of bleeding. Several other race horses have been similarly treated.

EXAMPLE 40

A male groom (32) had severe allergies and would wake up in the morning with swollen eyes and puffy face. He applied the solution of Example 1a directly into the nostrils at night before retiring. The following morning he awoke with none of the swelling of the eyes and face which he routinely suffered from. The treatment was repeated whenever necessary and was always effective.

Similar results were achieved in several other patients with similar allergy symptoms.

EXAMPLE 41

A man (63) had severe vertigo due to inflammation of the middle ear which did not respond to conventional treatment including several kinds of seasick pills. He placed the solution of Example 1a in his external ear canal and a few hours thereafter used the solution, diluted one tablespoon to one ounce of water, as a gargle in the evening before retiring. The following morning the vertigo had disappeared.

EXAMPLE 42

A female (48) with symptoms similar to those of Example 41 was given the same treatment, with the exception that she did not instill the medication in the external ear canal. The solution of Example 1a was used as a gargle diluted as before one tablespoon (15 cc) in one ounce (30 cc) water. The following morning, there were no symptoms.

This gargle treatment has been used by many people for sore throat or with systemic flu-like symptoms with consistent benefit.

The following examples illustrate the use of the compositions of this invention for the treatment of herpes lesions.

EXAMPLE 43

The topical application of the solution of Example 1a to an 8 year old boy with anal herpes resulted in their disappearance. The condition recurred after a few months and a repeat of the topical application of the solution again resulted in a prompt disappearance of the perpetic lesions.

EXAMPLE 44

The solution of Example 1a was applied to the lesions of a male (32) with genital herpes topically several times (3-4) a day. The lesions disappeared in a few days.

EXAMPLE 45

A male (59) with recurrent herpes labialis applied the solution of Example 1a to the lesions as soon as a raised inflamed area appears. The lesion does not fully develop but instead disappears.

EXAMPLE 46

A male (44) developed severe intercostal herpes, possibly zoster. The topical application of the solution of Example 1a resulted in a disappearance of the lesions.

EXAMPLE 47

A female (40) with herpes of the eye had a lesion in the internal canthus (inner corner of the eye). The lesion was a crusted lesion present for two days. The topical application of the solution of Example 1a caused a prompt disappearance of the lesion.

EXAMPLE 48

A male (73) developed herpes of the inguinal nerve in the groin. The solution of Example 1a was applied topically daily, which caused a rapid disappearance of the lesions. A pigmented area remained at the site but this also disappeared after several months.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the amelioration of deep or intractable pain which comprises applying topically proximate the situs of the pain an analgesically effective amount of an aqueous mixture comprising in a pharmaceutically acceptable carrier, biphenamine at a concentration of up to 1% by weight, and a topically acceptable skin penetrant selected from the group consisting of DMSO, at a concentration of less than 10% by weight, and propylene glycol, the concentrations of biphenamine and skin penetrant in the mixture being ineffective to ameliorate the pain when applied separately from the other to the situs.

2. A method according to claim 1 wherein the mixture is applied to the skin.

3. A method according to claim 2 wherein the mixture is applied to burned skin on successive occasions.

4. A method according to claim 1 wherein the skin penetrant is propylene glycol.

5. A method according to claim 4 wherein the biphenamine is present in the mixture as the hydrochloride salt thereof at a concentration of about 0.1% to 1% and the propylene glycol is present at a concentration of about 5% to 15%.

6. A method according to claim 5 wherein the propylene glycol is present at a concentration of about 10%.

7. A method according to claim 6 wherein the mixture is applied to the skin.

8. A method according to claim 7 wherein the mixture is applied to burned skin on successive occasions.

9. A method according to claim 1 wherein the pain is joint pain caused by a diseased or traumatized bone joint.

10. A method according to claim 9 wherein the pain is joint pain caused by rheumatoid arthritis.

11. An analgesic composition adapted for topical administration and comprising an aqueous mixture of biphenamine, at a concentration of up to 1%, and propylene glycol, the concentrations of propylene glycol and biphenamine in the composition being collectively effective to render the composition capable of ameliorating deep or intractable pain when the composition is applied topically proximate the situs of the pain but ineffective for either component of the composition to do so in the absence of the other.

12. A composition of claim 11 wherein the concentration of the propylene glycol therein is about 5% to 15%.

13. A composition of claim 11 wherein the biphenamine is present as the hydrochloride salt thereof at a concentration therein of about 0.1%.

14. A composition of claim 13 wherein the concentration of the propylene glycol therein is about 5% to 15%.

* * * * *